United States Patent [19]
Wilson, Jr. et al.

[11] Patent Number: 5,482,463
[45] Date of Patent: Jan. 9, 1996

[54] ANTI-SLIPPAGE MECHANISM FOR DENTAL IMPLANT COMPONENTS

[76] Inventors: Richard S. Wilson, Jr., 1416 Burmont Ave., Havertown, Pa. 19083; Kenneth C. Wenzer, 11538 February Cir., #402, Silver Spring, Md. 20904; Barry F. Sukoneck, 935 Remington Rd., Wynnewood, Pa. 19096

[21] Appl. No.: 224,872

[22] Filed: Apr. 8, 1994

[51] Int. Cl.⁶ ..................................................... A61C 8/00
[52] U.S. Cl. ........................................... 433/173; 433/174
[58] Field of Search ..................................... 433/172, 173, 433/174, 175, 176, 177

[56] References Cited

U.S. PATENT DOCUMENTS

| | | | |
|---|---|---|---|
| 5,040,982 | 8/1991 | Stefan-Dogar | 433/173 X |
| 5,040,983 | 8/1991 | Binon | 433/173 |
| 5,049,073 | 9/1991 | Lauks | 433/173 |
| 5,071,351 | 12/1991 | Green, Jr. et al. | 433/173 |
| 5,104,318 | 4/1992 | Piche et al. | 433/173 |
| 5,145,371 | 9/1992 | Jorneus | 433/173 |
| 5,336,090 | 9/1994 | Wilson, Jr. et al. | 433/173 X |

*Primary Examiner*—Nicholas D. Lucchesi
*Attorney, Agent, or Firm*—Robert Halper

[57] ABSTRACT

To prevent loosening of screw joints for dental implant component stacks, a spring washer is placed directly beneath the head of a gold screw in a circular channel of a gold cylinder. Other joints such as between the gold cylinder and its abutment and between the abutment and the fixture can also be equipped with spring washers.

3 Claims, 3 Drawing Sheets

ANTI-SLIPPAGE MECHANISM FOR DENTAL IMPLANT COMPONENTS

FIELD OF THE INVENTION

This application is an extension of my co-pending application Ser. No. 159,326 filed on Nov. 30, 1993 titled Transmucosal Healing Cap and Lockwasher for Dental Implants. Whereas the former application was concerned with seating and fixing into place of the healing cap placed in the interval between surgery and abutment/prosthesis fabrication and the use of washers therewith, this application has as the main goal a spring washer and modifications to the current commercially available dental implant components by the use of certain types of washers which provide improved resistance to slippage of screw joints. A second goal of the invention is to achieve the first goal with minimal modifications to current practice.

BACKGROUND OF THE INVENTION

The general procedure in fabricating permanent restorations in current dental implant practice is as follows. The fixture is the component which is surgically placed into the jawbone; this is often accomplished by a periodontist or oral surgeon. After a healing period of 3–6 months, during which a process of bone growth around the fixture called osseointegration occurs, the implant is exposed. A general dentist or prosthodontist then performs the restoration, which involves placement of an abutment of a specific size and shape over the fixture and securing the same by means of a bolt threaded into a cavity in the fixture. The implant distal surface contains a flat, polished outer ledge and a central hex which is then engaged by a tool during placement. Also indicated by the prior art is a submucosal healing cap and a transmucosal healing cap which prevent the fixture from becoming infiltrated with tissue from the gingiva and/or bone. In addition to keeping tissue out of the fixture the healing cap establishes a sulcus or opening above the fixture to allow placement of the second component, the abutment.

The abutment is secured into the threaded cavity of the fixture by a titanium bolt, called the abutment retaining screw. The prosthesis is the third component of the system; this element is fabricated of cast gold alloy and porcelain. However, since machined parts have greater accuracy than cast parts, the prosthesis is commonly cast to a machined component called the gold cylinder. This gold cylinder, as part of the completed prosthesis, is fastened to a threaded cavity in the abutment retaining screw by the gold screw. This gold screw, being smaller and of weaker alloy than the titanium abutment retaining screw, should normally be the first to fracture if excessive force is encountered.

One modification of the above system is to attach the prosthesis directly to the fixture without any intervening abutment. This method is termed the UCLA modification and uses only the large titanium screw.

A further variation is to cement a restoration to implants in the same manner as is done in conventional fixed bridges on natural teeth. In this case, a tapered abutment without threads, often referred to as a cementable abutment, is fastened to the fixture with a large titanium abutment retaining screw. Thus, this method also has only one screw in the system.

To summarize, implant dentistry relies upon screws to fasten together component stacks. These stacks consist of the fixture, abutment, and prosthesis (commonly fabricated around a machined gold cylinder). A second possibility consists of just the fixture and prosthesis (UCLA), eliminating the abutment for reasons of esthetics, angulation, etc. A third possibility consists of an abutment to which the prosthesis is cemented.

Screws used as fasteners can loosen when subjected to cyclic or vibratory loads. Such loads certainly occur in the mouth. This loosening can be viewed more accurately as slippage of the entire joint, which consists of the two components involved and their fastening screw.

Consequences of screw loosening in the general case are:

1) Repeated loosening of the restoration. If the frequency is months or weeks the loosening becomes unacceptable to both the patient and the dentist.

2) Gold screw or abutment retaining screw bending.

3) Gold screw or abutment retaining screw fracture.

While these problems with the fastener do not occur in the majority of implant cases, their frequency is sufficient that the causes are being actively investigated.

In some instances, the system is overloaded, for instance by placing too few implants for the number of teeth being replaced. In these cases, gold screw fracture or bending is the most preferable outcome, because it gives the clinician warning that the system is being overloaded. Gold screw bending or fracture is less of a problem than abutment retaining screw bending or fracture, since the gold screw is most easily retrievable. Abutment retaining screw fracture can be dealt with by removing the fragment of the abutment retaining screw contained within the threaded cavity in the fixture. This procedure is usually difficult and can even irreversibly damage the fixture. Fixture fracture or failure of osseointegration is the least desirable outcome of overload, as these imply loss of the fixture. If the gold screw breaks, there is still time to reconsider the placement of fixtures and the design of the prosthesis and make corrections, perhaps by adding more fixtures.

Screws are also known to loosen in many cases that are well designed, have sufficient fixtures and appear to fit very accurately. These instances of screw loosening are due to vibration, defined as low but highly repetitive forces on the joint. Vibration has a tendency to loosen bolts and screws. It has been postulated that very small movements of the implant prosthesis, termed micromovements, occur in response to vibration and increase the chance of screw loosening. This is at least part of the motivation to cement restorations; note, however, that there is still a screw in the cementable abutment.

When a screw is tightened, a tensile force, termed the PRELOAD, is built up in the screw, mainly between the head and the first few threads. This preload is what holds the components of an implant component stack together. The screw is placed in tension, and the components fastened by the screw are placed in compression. Preload also prevents loosening of the screw. The preload should be as high as possible (for a given tensile strength of the screw material) and should fluctuate as little as possible to prevent loosening.

Occlusal forces from chewing, speaking, bruxing, etc. (which can be viewed as vibrations) load the prosthesis and place forces on abutment retaining screws and gold screws which may result in loosening of the screws. If the screw loosens, the preload is decreased or lost, the screw joint opens up, and the screw will then loosen further, bend or break. Once permanent deformation takes place, either through wear-and-tear effects or through gross bending, there is nothing to prevent the screw from loosening.

Additional effects act on screws to reduce preload. When any implant screw is tightened for the first time, contact between its threads and the screw channel walls only occurs on microscopic areas of roughness. Plastic flow of these initial contact points occurs and reduces preload. This phenomenon is called embedment relaxation or settling effects. Thus, the torque used to place a retaining screw initially is greater than that required to remove it.

One proposed solution to screw loosening is using high torque or torque within a certain range in the placement of the various retaining screws. However, what constitutes the proper torque has not been determined by controlled scientific investigation. Also, the torque required to loosen an implant screw is less than that used to tighten it, due to settling effects and wear-and-tear effects on the screw threads. High initial torque may not prevent screw loosening months or years after placement, due to wear-and-tear effects and the cyclic loading that occurs in the mouth. Even if an ideal initial torque could be determined, it has been shown that dentists vary widely in their ability to place a screw within a specified torque range. Mechanical torque drivers are necessary to achieve consistency, but this application only relates to INITIAL torque values, not those achieved after settling effects and cyclic loading. Very high torque may create torsional stress on the screw beyond safe limits, leading to permanent deformation and fracture. Thus, placing screws with high torque is not an ideal solution to the problem of retaining screw loosening in well-designed implant cases.

Spring washers of the helical, split-lock type (hereafter simply called "lockwashers") and/or Belleville washers work on many levels to help prevent screw loosening. With respect to helical washers the descriptive material in my co-pending application Ser. No. 159,326 is hereby incorporated by reference.

A spring washer placed under the screw head maintains a constant tension in the screw, decreasing the chance of loosening under cyclic or vibratory loads. The spring washer acts as a damping mechanism for micromovement, preventing transmission of that movement into the screw.

Washers act to distribute loads and provide a surface for uniform torque control. By increasing the preload and the clamping forces, spring washers may make the screw joint more resistant to opening up and subsequently bending or fracturing.

Some of the kinetic energy of screw tightening is converted into potential energy in the spring of the washer; thus, spring washers store energy. This energy adds to the preload. Another way in which washers add to preload is more subtle. For hard metal screws and screw channels, up to 90% of the applied torque is used to overcome the friction forces caused by the screw threads and under the screw head. Washers represent dry lubrication. Reducing the coefficient of friction of the screw in its channel and/or under the screw head acts, according to the principles of operation of fasteners, to increase the preload of the screw for a given applied torque. Consequently, the possibility of loosening is decreased significantly. The increased preload also reduces the working stresses in the components held together by the screw, decreasing the possibility of fatigue failure due to cyclic stress.

The most favorable location of the spring washer in order to achieve this effect is on the screw journal just below the head. Also, the principles of operation of fasteners show that the preload is inversely related to collar size; thus having the screw head bear on the spring washer at the smallest possible diameter will give the greatest increase in preload. Note that the screw head can be of large diameter; the diameter of the bearing surface of the washer against the screw head is the factor which determines the preload. Belleville washers with their conical shape can accomplish this effect if they are placed on a screw at the journal, just under the head.

The effect of reducing the coefficient of friction and/or the collar radius of the screw head is to increase the preload for a given torque. This avoids the problems of extremely high torque placement of screws, which places high torsional stress on the screw and weakens it. In other words, for a given torque, one can have higher preload with a washer.

One final way of thinking about lockwashers is to examine what % of a full turn of a retaining screw it takes to dump all of the preload out of the system. In current implant practice, a very small turn of the screw, perhaps as little as $\frac{1}{32}$ of a turn, would be sufficient to eliminate most of the preload. With a lockwasher of appropriate torsional stiffness, a significant fraction of preload could be maintained even if the screw was backed off ¼ or ½ of a turn. This arrangement would allow more leeway, in terms of time, to intervene before loosening and damage took place.

One current example of an anti-slippage mechanism in dental implants is filed as serial number for patent pending Ser. No. 159326, filing date Nov. 30, 1993. This patent application shows a split-lock type lockwasher in various modifications placed between the healing cap and the fixture. An opening in the gingiva (gum) is created surgically and preserved by use of the healing cap body. The cap is intended to pass through the gingiva to the outer surface of the surrounding gingiva. The underside of the cap is shaped in various modifications to provide a cavity or flat surface which accepts a lockwasher. The lockwasher is of the split-lock, helical type. The cap is installed on the implant by threading a separate screw into the threaded base of the implant with the lockwasher in between until the proximal surface of the cap is in contact with the washer, which is in contact with the distal surface of the implant. The goal of healing caps in general is to shield the upper surface of the implant from overgrowth of gingival tissue and at the same time maintain an opening through the gingival tissue which overlies the implant. The novelty of this invention is to provide resistance to slippage so that the healing cap cannot loosen in response to muscular movements in the mouth.

It is an object of the current invention to design a gold screw/gold cylinder assembly and an abutment retaining screw/abutment assembly that will not loosen when used in a well-designed implant restoration.

It is a further object of this invention to prevent screw bending and/or fracture secondary to loosening.

It is still further an object of this invention to accomplish the first two objects for many if not all of the current commercially available implant component systems without major modifications to those systems.

SUMMARY OF THE INVENTION

The invention provides a screw joint for dental implant component stacks which has greater resistance to loosening, and therefore greater resistance to bending and/or breaking. This effect is accomplished by the use of spring washers and modifications to the screw and screw channel in implant components.

The gold screw is driven into a threaded channel in the abutment retaining screw, and the head of the gold screw fits in a channel within the gold cylinder and bears on a flat surface of the gold cylinder. The current invention widens both the radius of the gold screw head and the channel in the gold cylinder. A helical split-lock washer or Belleville washer is placed between the gold screw head and the flat bearing surface of the gold cylinder. This has the effect of increasing the preload and of increasing resistance to slippage of the entire joint, for the reasons discussed above.

Many types of spring washers exist. These include helical split-lock, Belleville (also called coned-disk springs), curved, wave, finger, and slotted. With respect to helical washers the descriptive material in my co-pending application Ser. No. 159,326 is hereby incorporated by reference. Split-lock or Belleville washers are preferred in the current application because they apply uniform pressure around their entire radius and because they can be designed to be compressed flat and maintain their tension. They also would not scratch the bearing surfaces of implant components. While Belleville washers are preferable, other types of spring washers as described above can be used.

The current invention concerns the gold screw/gold cylinder joint, because this is the joint that most often loosens in function. The same concept may be applied to the abutment retaining screw/abutment joint. This is particularly important in the cases of the UCLA abutment and the cementable abutment, because the abutment retaining screw is the only screw in the system and is therefore prone to loosening.

DETAILED DESCRIPTION OF THE INVENTION

Figure 1:
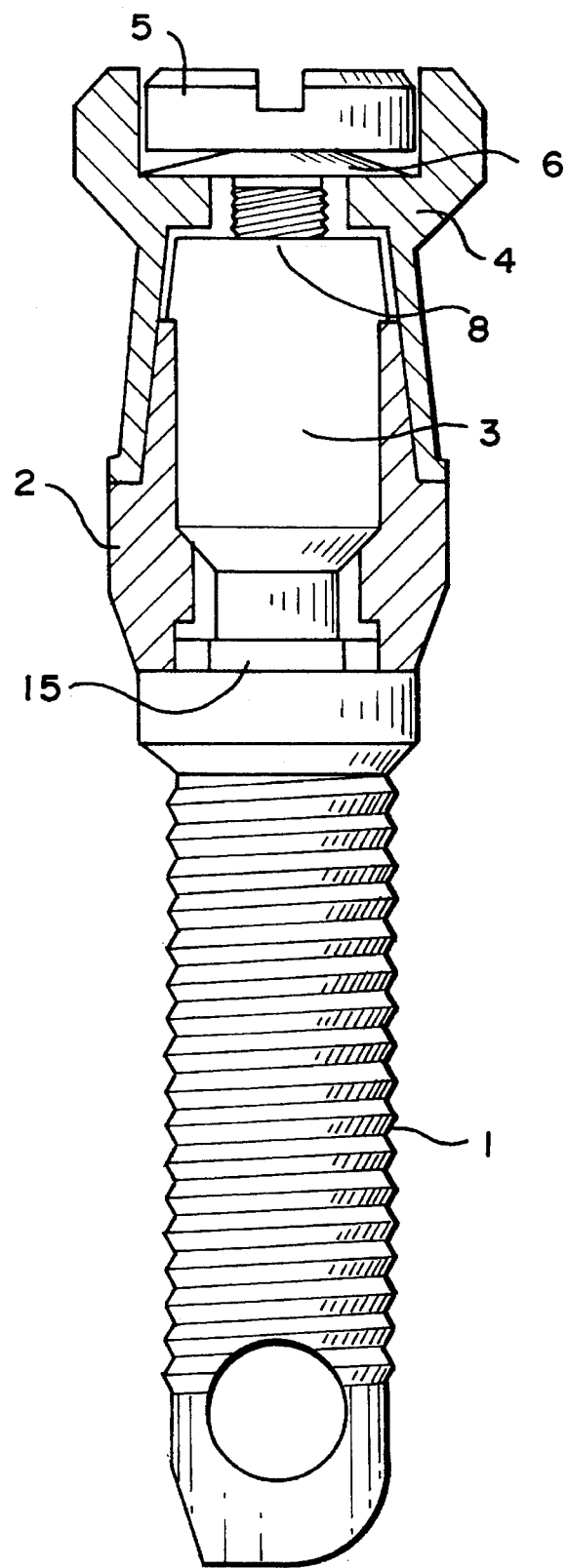
FIG. 1 is a sectional view of an assembled component stack.
Figure 2:
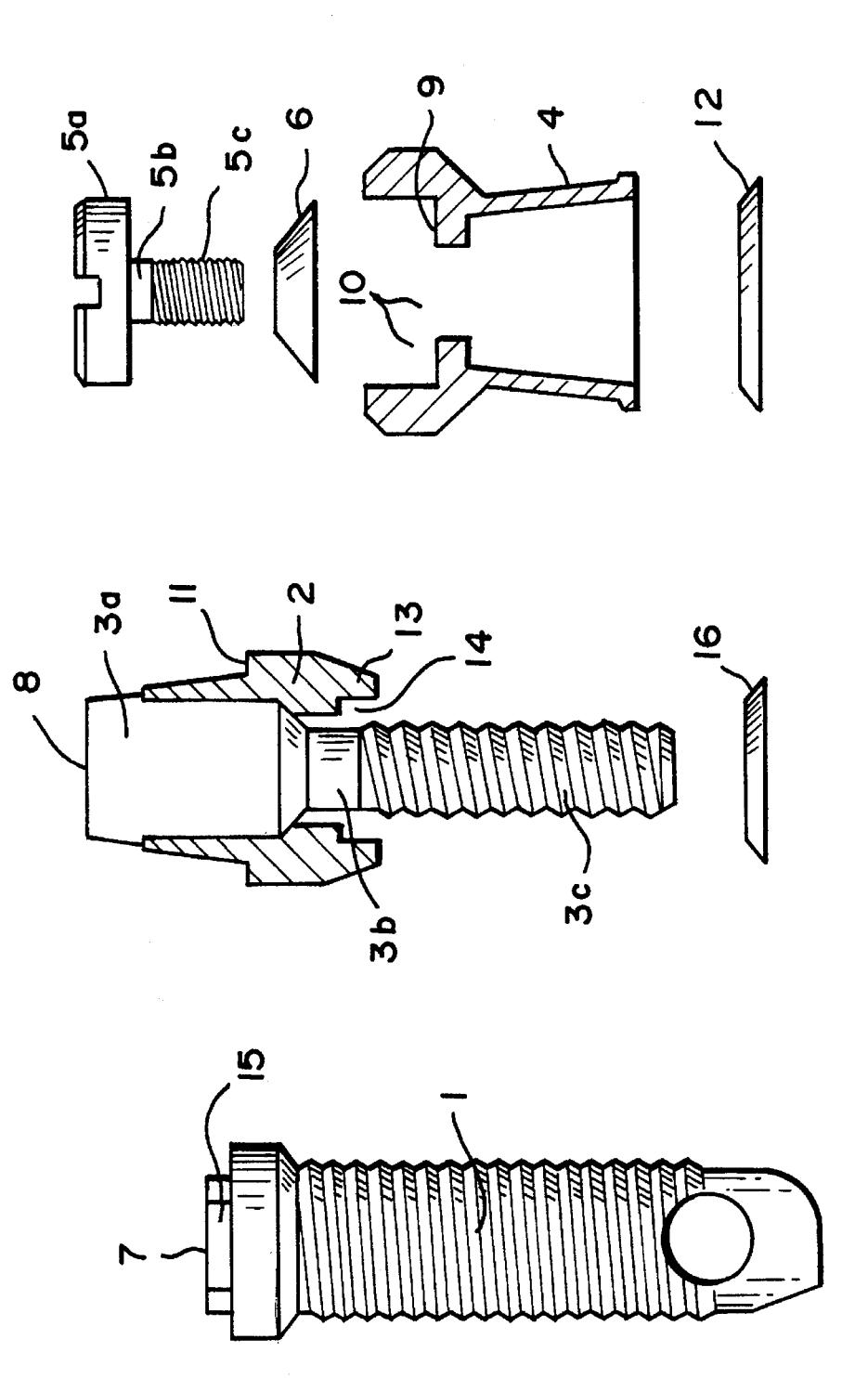
FIG. 2 is a frontal view of a disassembled component stack.
Figure 3:
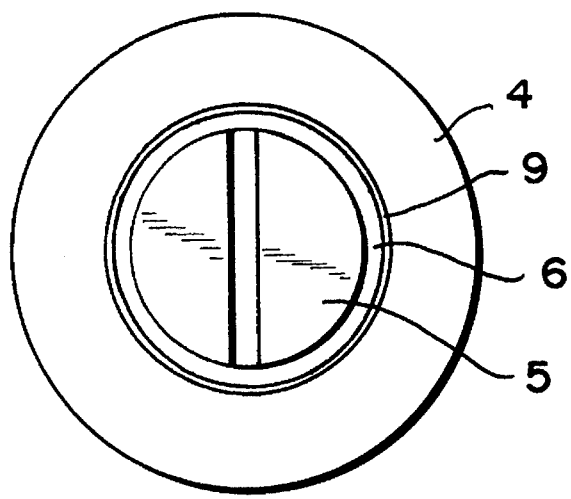
FIG. 3 is a plan view taken on line I—I of FIG. 1.

The device as seen in FIGS. 1 and 2 consists of a special gold cylinder, gold screw and Belleville washer. The fixture 1, abutment 2, and abutment retaining screw 3 are to be considered as generic examples of these components.

The gold screw 5 fastens the gold cylinder 4 to the threaded cavity 8 in the abutment retaining screw 3. This action places the gold cylinder 4 in compression against the abutment 2. In common with all screws, the gold screw has three parts which contribute to its function. One part is the head 5a, which is slotted or hexed to accept screw drivers and which bears on the gold cylinder. The second part is the journal 5b, the non-threaded part extending between the head and the first thread. The third part is the threaded section 5c which engages the corresponding threaded cavity 8 in the abutment retaining screw 3. The abutment retaining screw also has a head 3a, a non-threaded journal 3b and a threaded section 3c. The threaded section threadingly engages a threaded cavity 7 in the fixture.

The gold screw head 5a fits loosely into a channel 10 in the gold cylinder 4. A Belleville washer 6 is fabricated from a suitable material, such as gold alloy or titanium. It is fabricated such that the opening 6a at the apex of the cone is very slightly larger in diameter than the threads 5c of the screw. It is further fabricated such that the diameter of the base of the cone 6b is slightly smaller than the diameter of the gold cylinder channel 10. The base 6b bears on a flat surface 9 of the gold cylinder 4.

In practice, the procedure and action of the mechanism would be as follows. When the prosthesis is placed, the Belleville washer is placed on the gold screw shaft at the journal. The gold screw is then placed in the channel in the gold cylinder and is further placed so as to engage the threaded cavity in the abutment retaining screw. As the gold screw is turned, the Belleville washer compresses and its outer diameter expands; the slightly larger inner diameter of the gold cylinder channel accommodates this expansion. The Belleville washer may be compressed to flat. The gold cylinder channel is then plugged with putty and composite resin materials in the usual manner. The screw joint is now extremely resistant to loosening when used in a properly designed implant restoration.

Figure 4:
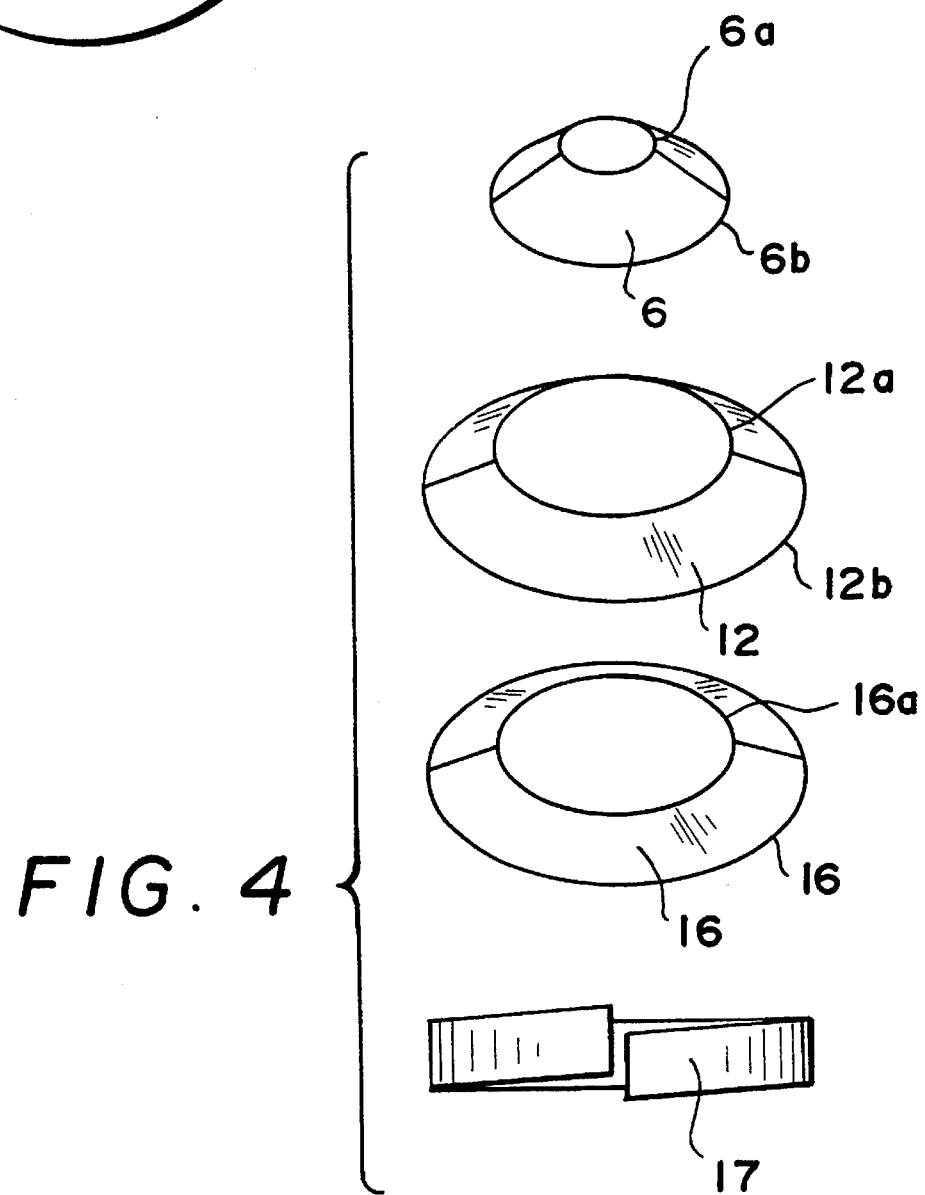
FIG. 4 are details of other Belleville washers and other suitable washers.

The washer could also be placed between the gold cylinder 4 and the abutment 2. The abutment has a trapezoidal shape from its top to the medial region. Extending outwardly from the base of the trapezoid is a planar surface 11. The proximal surface of the gold cylinder fits squarely over this surface. A Belleville washer 12 has an opening 12a at its apex shaped to fit over the trapezoid and a diameter 12b at its base slightly smaller than the diameter of the planar surface so that when the gold screw is torqued, the washer will flatten and extend to the outer diameter of the planar surface. Similarly the proximal surface of the abutment is defined by a pair of tapered legs 13 that enclose a circular channel 14. Within this channel nestles a hexagonal fitting 15 that is located on the distal surface of the fixture and contains the aforementioned threaded cavity 7. Between the legs of the abutment and the exterior surface of the fixture below the fitting another Belleville washer 16 can be placed. This washer again differs from the preceding described washers only dimensionally and has an opening 16a at its apex and a diameter 16b slightly smaller than the outer diameter of the abutment legs and the fixture between which it is placed. FIG. 4 depicts views of the Belleville washers 12 and 16 as well as other spring washers that might be used in lieu of the Belleville washer, such as the helical split lock washer 17, to prevent slippage. While these locations are theoretically less favorable than under the screw head, the fact that a larger washer is necessary may provide a mechanical advantage. Washers in these locations must fulfill two requirements. They must not scratch the components and they must form a seal by compressing flat.

It should be understood that while the invention has been described with considerable specificity, various modifications and arrangements could be made without departing from the scope of the invention as expressed by the appended claims.

We claim:

1. An implant component stack having a specially designed screw joint, said rack comprising:

a) an implantable fixture, an abutment and a gold cylinder, said cylinder having a circular channel;

b) a vertical axis coincident and extending through said fixture, abutment and gold cylinder;

c) a gold prosthesis retaining screw having a grooved head, a non-threaded journal and a threaded section;

d) a spring washer (made from material selected from the group consisting of titanium and gold alloy) that provides resistance to loosening of said screw joint, uniform pressure around its radius, maintenace of tension and which flattens out when said gold screw is torqued;

e) said cylinder having a proximal surface and a distal surface, said prosthesis retaining screw head nestling (loosely) In said circular channel adjacent said distal surface, said washer underlying said grooved head and having an outer diameter just smaller than the diameter of said channel and an inner opening just larger than the diameter of said retaing screw; (said inner opening surrounding said retaining screw in the region of said non-threaded journal)

f) said abutment having a central opening coincident with said axis and a proximal surface and a medial surface, said medial surface underlying said proximal surface of said gold cylinder, said abutment proximal surface including a pair of tapered legs that enclose a channel in alignment with said vertical axis;

g) an abutment retaining screw extending through said opening in said abutment and having a central threaded cavity for receiving said gold prostehsis retaing screw, a non-threaded journal below said cavity followed by a threaded section;

h) said fixture having a distal surface and a proximal surface, said proximal surface of said abutment overlying said distal surface of said fixture, a threaded hexagonal fitting on said distal surface of said fixture, said threaded section of said abutment retaining screw fitting into said fixture;

wherein said abutment (has) further includes a first region that fits into said gold cylinder and (has) a medial region that has a planar surface extension and between said proximal surface of said gold cylinder and said planar surface extension (in which) a second washer is located.

2. An implant component stack as in claim 1 wherein a third washer is placed between said legs of said abutment and said distal surface of said fixture below said enclosed channel.

3. An implant component stack 2 as in claim 2 wherein said washers are Belleville conical washers.

* * * * *